United States Patent [19]

Bass et al.

[11] Patent Number: 5,451,862
[45] Date of Patent: * Sep. 19, 1995

[54] SYSTEM AND METHOD OF USE FOR CONDUCTING A NEUTRAL CORROSION SURVEY

[75] Inventors: Craig D. Bass, Monroeville, Pa.; Richard D. Valenti, Jr., Fayetteville, N.Y.; Emer C. Flounders, Jr., Abington, Pa.

[73] Assignee: Henkels & McCoy, Inc., Blue Bell, Pa.

[*] Notice: The portion of the term of this patent subsequent to Sep. 13, 2011 has been disclaimed.

[21] Appl. No.: 258,388

[22] Filed: Jun. 10, 1994

Related U.S. Application Data

[63] Continuation of Ser. No. 942,688, Sep. 9, 1992, Pat. No. 5,347,212.

[51] Int. Cl.$^6$ .............................. G01R 19/00
[52] U.S. Cl. ........................ 324/67; 324/544
[58] Field of Search ............... 324/66, 67, 509, 510, 324/522, 523, 539, 541, 543, 544, 713, 715; 379/26

[56] References Cited

U.S. PATENT DOCUMENTS

| | | | |
|---|---|---|---|
| 3,289,076 | 11/1966 | Edis et al. | 324/67 |
| 3,792,350 | 2/1974 | Bossler et al. | 324/530 |
| 3,991,363 | 11/1976 | Lathrop | 324/67 |
| 4,697,137 | 9/1987 | Haddon et al. | 324/512 |
| 4,839,598 | 6/1989 | Calvert et al. | 324/539 |
| 4,947,469 | 8/1990 | Vokey et al. | 324/523 |

FOREIGN PATENT DOCUMENTS 9011553 10/1990 WIPO ................. 324/543

OTHER PUBLICATIONS

Maloney, Charles A.; "Locating Cable Faults"; Jul. 1973, IEEE Trans. On Industry Apps.; vol. 1A-9, No. 4, pp. 380-394.

Primary Examiner—Kenneth A. Wieder
Assistant Examiner—Christopher M. Tobin
Attorney, Agent, or Firm—Caesar, Rivise, Bernstein, Cohen & Pokotilow, Ltd.

[57] ABSTRACT

A system and method for testing underground electric cables, while in service, for active corrosion and degree of neutral loss. The method is conducted by applying a non-harmonic selected frequency signal to the neutral(s) of the underground cable connecting a pair of structures, e.g., power transformers, from a variable frequency generator of the system. The test is conducted by a surveyor wearing foot electrodes which contact the earth as the surveyor walks along the earth over the cable in a close interval steps. At each step, direct current (DC) potentials are monitored by a voltmeter between a copper-copper sulfate electrode carried by the surveyor and brought into contact with the ground at each step and the transformer ground. The potential of the gradients between the foot electrodes at the selective frequency and at the native alternating current (AC) is also measured by the voltmeter. These measurements are recorded at a stationary location on a digital data logger and/or computer. At all points of direct current or selective frequency potential abnormalities, a waveform is recorded of both potentials, as well as peak-to-peak potential measurements, maximum potential, minimum potential, mean potential, frequency, rms voltage, and soil resistivity to generate a continuous corrosion and condition profile of the entire length of cable including permanent land features.

24 Claims, 2 Drawing Sheets

SYSTEM AND METHOD OF USE FOR CONDUCTING A NEUTRAL CORROSION SURVEY

This invention is a continuation application of U.S. patent application Ser. No. 07/942,688, filed on Sep. 9, 1992, now U.S. Pat. No. 5,347,212.

BACKGROUND OF THE INVENTION

This invention relates generally to measuring and testing systems and methods-of use, and more specifically to systems and methods of use for testing of underground bare neutral conductor electric cable, without removing the electric cable from operation, to detect active corrosion, harmonic distortion, metal loss of the bare concentric neutrals, and grounding anomalies that are detrimental to the safe and efficient operation of the underground electric distribution system.

Since the early 1960's electric cable has been installed underground throughout the United States. This electric cable was originally installed with bare concentric electric neutrals. The purpose of the bare neutral was to provide a safe path for the flow of the cable's rated current during fault conditions resulting either from cable failure and/or third party damage. Further, the bare neutrals provide additional grounding in high resistivity soil, an equipotential environment to reduce electric stress on the cable, and shielding of the cable's electric field.

Within a few years of installation, problems began to arise from corrosion of the bare neutrals. Failures of these neutrals were reported in many earth environments and under numerous service conditions. To mitigate the corrosion of bare neutral underground cable, classical corrosion direct current potential surveys were conducted in conjunction with the subsequent installation of cathodic protection. After years of corrosion mitigation efforts, it became apparent that conventional corrosion survey techniques were ill suited for the detection of areas of corrosion and neutral loss. Conventional corrosion surveys were found to miss actual areas of corrosion while at the same time indicating corrosion where no corrosion existed.

In the mid 1980's as a result of the poor corrosion resistance of bare neutral underground electric cable, companies began to install sheathed neutrals on all new underground electric transmission and distribution electric cables. During the period prior to the adoption of sheathed electric cable, millions of miles of bare neutral cable were installed in the United States. Electric companies have been searching for a method to identify the corrosion problems on underground electric cables as well as the areas were the neutrals are damaged without removing the electric cables from service. No method to date has been effective in accomplishing these tasks economically and with a degree of reliability necessary to prevent power service interruption.

For example, in U.S. Pat. No. 4,839,598 (Calvert et al.) there is disclosed a system for detecting breaks in the bare neutral conductors of an underground cable. The system entails taking the cable out of service so that its neutral conductor and phase conductor (i.e., a main power conductor) are connected together at one end of the cable, while an alternating test signal is applied across the neutral conductor and the phase conductor at the other end of the cable. The electrical potential of the alternating signal is measured at a series of spaced apart points on the earth's surface along the cable's path. The potential between those points over a cable section with an open in the neutral conductor will be about two orders of magnitude greater than the potential between points above a good cable section. The system disclosed in the aforementioned patent is also the subject of an article entitled Overground Method Pinpoints Concentric-Neutral Corrosion, by Donald K. Baver, appearing in Transmission & Distribution, July 1989, pp.48-54.

One of the drawbacks of the prior art, like that described above, is the requirement that the electric cable be removed from service during the testing. Another drawback is that it does not establish percentage of allowable neutral loss, i.e., while the prior art method locates breaks in the neutrals, it does not determine the degree of metal loss where corrosion protection may be applied to mitigate any further corrosion damage prior to the need for cable replacement. Another drawback of the prior art is that it does not employ a concurrent direct current potential survey to correlate areas of active corrosion versus areas of other grounding abnormalities. Finally the existing method does not employ waveform analysis of the alternating current in the conductor and earth to detect 60 Hertz harmonic activity and half wave rectification which is not corrected may lead to further cable damage of either cathodically protected existing cable or replacement cable.

OBJECTS OF THE INVENTION

Accordingly, it is a general object of the invention to provide a system and method of use which overcomes the disadvantages of the prior art.

It is a further object of this invention to provide a system and method of use which enables the detection of various characteristics of the neutral(s) of an underground electric cable, while the cable is in service.

It is a further object of this invention to provide a system and method of use which enables a surveyor to walk along the ground located over an underground cable to bring various probes into contact with that ground at predetermined spacing to effect the detection of various characteristics of the neutral(s) of the underground electric cable, while the cable is in service.

It is still a further object of this invention to provide a system and method of use for detecting areas of active corrosion, neutral damage, degree of neutral loss, type of grounding abnormality, waveform analysis of harmonic and rectification activity, to facilitate a subsequent cable rehabilitation program.

It is a further object of the invention to provide a system and method for automatically deriving data indicating the degree and location of corrosion at all points along a tested underground cable.

It is still a further object of the invention to provide a system and method for automatically deriving data indicating the degree and location of corrosion at all points along a tested underground cable in a continuous profile generated graphically from the derived data.

It is a further object of the invention to provide a system and method for automatically evaluating data for corrosion protection and rehabilitation of any damaged cable by an expert system analysis of the autologged data.

SUMMARY OF THE INVENTION

These and other objects of this invention are achieved by providing a system and method of use for testing the status of at least one neutral conductor of an underground electrical cable forming a portion of an electrical distribution system while the cable is in service. The cable comprise at least one neutral conductor and at least one primary conductor carrying AC current therethrough. The neutral conductor of the cable is connected between a pair of electrically grounded structures, e.g., power transformers.

The system comprises a first means for impressing an electrical test signal of a predetermined frequency between the grounded structures to impress the signal on the neutral conductor while leaving the neutral conductor connected to the structures. A pair of electrically conductive probes are provided and arranged to be brought into contact with the ground located over the underground cable at relatively closely spaced intervals. Monitoring means is coupled to the pair of electrically conductive probes, e.g., foot mounted electrodes, for measuring the voltage gradients produced by the test signal in the ground while the probes are in contact with the ground at closely spaced intervals and while the primary conductor is carrying the AC current therethrough.

In accordance with one aspect of the subject invention the monitoring means in cooperation with the electrically coupled probes also measures the potential gradient produced in the ground by the native AC current.

In accordance with another aspect of the subject invention another probe is coupled to the monitoring means to measure the DC potentials at the closely spaced intervals.

In accordance with yet another aspect of this invention the resistivity of the soil contacted by the probes is measured.

In accordance with a most preferred embodiment of the method of this invention the foregoing measurements are utilized by the system to provide a continuous corrosion and condition profile of the entire length of cable including permanent land features.

DETAILED DESCRIPTION OF THE PREFERRED EMBODIMENT

Figure 1:
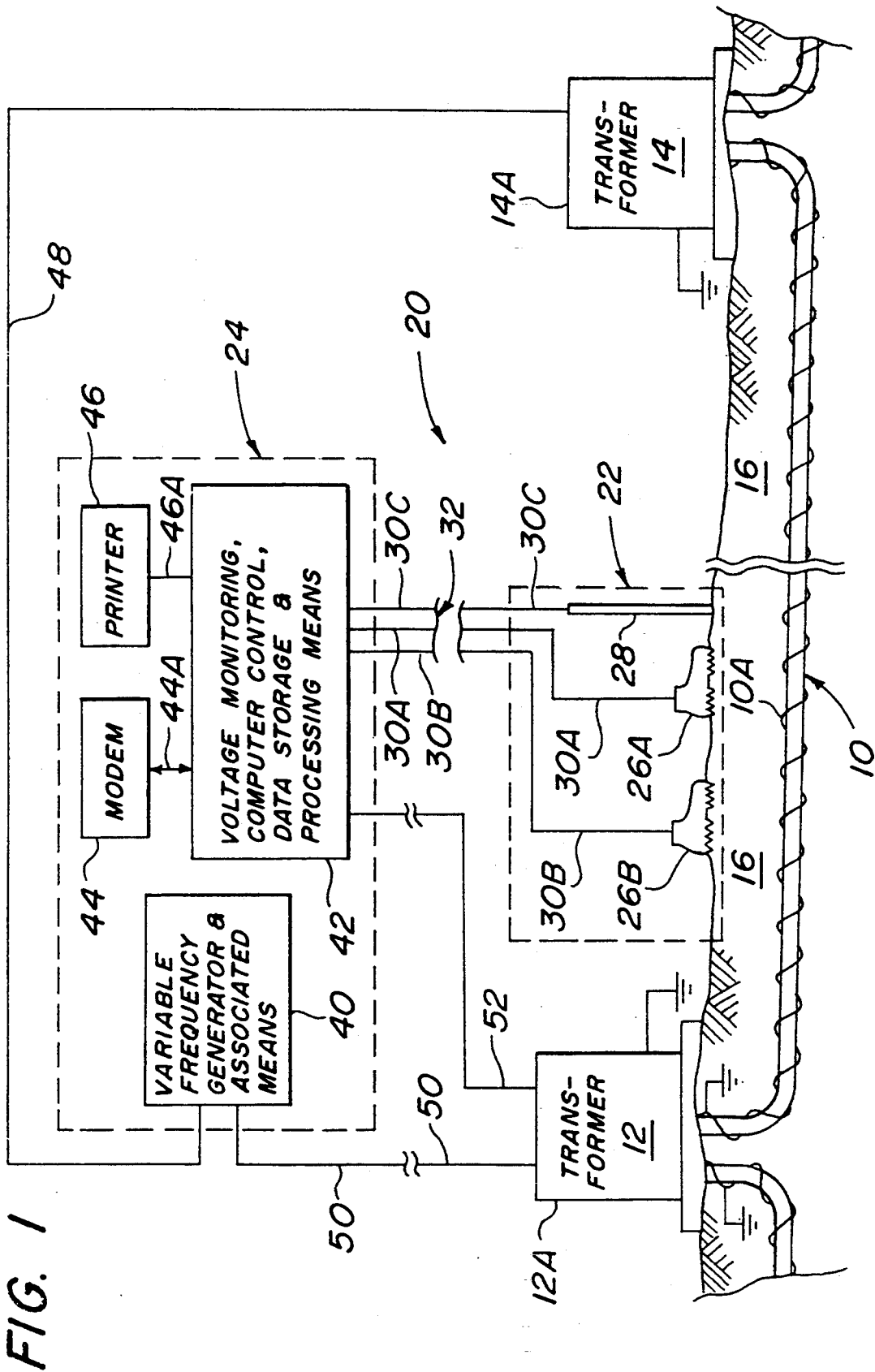
FIG. 1, constitutes a functional block diagram and partial schematic diagram of the system of the subject invention shown in use testing the neutral conductor(s) of a typical electrical power distribution system utilizing an underground cable.

Referring to the various figures of the drawing wherein reference numbers refer to like parts there is shown in FIG. 1 a system 20 and method of use for testing the neutral conductor(s) of an underground cable 10 of an electrical distribution system without having to remove the cable from service. In FIG. 1 a portion of a typical electrical distribution system is shown. That system basically comprises a pair of transformers 12 and 14 which are housed in respective grounded housings or vaults 12A and 14A, respectively. The transformers are serviced by the cable 10. That cable is buried in the ground (soil) 16 and includes one or more primary or phase conductors (not shown) interconnecting the transformers, and plural, bare neutral conductors 10A which are disposed concentrically, e.g., spirally, about the length of the cable. The neutrals 10A are connected to the grounded transformer housings 12A and 14A. It must be pointed out at this juncture that the electrical distribution system shown in FIG. 1 is merely exemplary of various types of power distribution systems utilizing various structures connected by various types of underground cables having one or more neutrals (bare or insulated, concentric or not), in which the system 20 of this invention can be used.

The system 20 basically comprises a transportable ground potential sensing unit 22, and a test signal generating and monitoring station 24. The station 24 is arranged to provide a test signal on the neutral conductor(s) 10A of the buried cable 10 without having to remove the cable from service. This test signal induces what may be considered to be a "fault condition", but of low current so as not to damage the cable sheathing but sufficiently high to create potential gradients indicating actual neutral conductor conditions. The sensing unit 22 is arranged to be worn and/or carried by a person, e.g., a surveyor (not shown), walking over the earth 16 over the cable 10 to detect the induced potentials or gradients at predetermined spaces or steps, e.g., at 2.5 foot intervals, between the transformers 12 and 14, and to provide electrical signals indicative of those potentials via conductors, to be described later, to the monitoring station 24. Moreover, the unit 22 also provides electrical signals indicative of the DC potential between the end of the cable 10 at the starting point of the survey, e.g., transformer 12, and the position of the surveyor over the cable at the particular point along the cable's path.

The ground potential sensing subsystem 22 basically comprises a pair of shoes 26A and 26B and a conventional copper sulfate reference electrode or half cell 28. The shoes are arranged to be worn on the feet of the surveyor, and each shoe includes plural electrically conductive tines or prongs, e.g., 4130 chrome-molly steel electrodes, which dig into and make electrical contact with the soil 16 as the surveyor walks over the cable 10 between the transformers to conduct the survey. The prongs of the shoes 26A and 26B are electrically connected to electrically conductive wires 30A and 30B, respectively, to a junction box (not shown) worn on a belt by the surveyor. The junction box is connected to a shielded, twisted, three conductor cable 32. The cable 32 includes respective conductors 30A and 30b which are extensions of the wires from the shoes 26A and 26B.

The prongs of the shoes 26A and 26B sense the electrical potential gradients in the soil between the shoes. In accordance with the teachings of this invention, and as will be described in detail later, these potential gradients represent the potential gradients resulting from the impression of a test signal of a predetermined frequency on the neutral(s) 10A, and also represent the potential gradients resulting from the electrical power carried by the primary conductor of the cable at the native AC frequency, e.g., 60 Hz.

The reference electrode 28, serves to enable the measurement of the DC potential between the point at which the surveyor is located and the starting point of the survey, e.g., the grounded transformer housing 12A. To that end the electrode 28 is of preferably conventional construction and basically comprises an elongated tubular member formed of an electrically insulating material and having a pure electrolytic copper rod extending therethrough. A saturated solution of copper sulfate is located within the tube and in contact with the copper rod. The tip of the rod is porous and arranged to be brought into contact with the ground 16 by the surveyor at various points, e.g., at the 2.5 foot intervals, along the path between the transformer 12 and the transformer 14. The copper core of the reference electrode 28 is connected via an electrical conductor 30C to the surveyor's belt mounted junction box and from there through a corresponding wire 30C of the shielded cable 32 to the station 24.

The station 24 is transportable so that it can be located adjacent the starting point of the survey, e.g., the transformer 12. If desired the station can be moved to various positions between the transformers 12 and 14. To expedite its location, the station 24 is preferably mounted in a vehicle, although it is contemplated that it (or a portion of it) may be carried by the surveyor.

The station 24 basically comprises a variable frequency generator and associated means 40, a voltage monitoring, computer control, data storage, and processing means 42, a modem 44, a printer 46, and a test conductor 48. The variable frequency generator includes a terminal connected to an electrically grounded line or conductor 50 which is in turn connected to the grounded transformer housing 12A. The generator 40 also includes a "test signal output" terminal which is connected to one end of the test conductor line 48. The test conductor is a thin wire, e.g., from #18AWG to #2AWG depending upon the distance of the cable run (i.e., the distance between transformers 12 and 14) and is disposed on a reel (not shown) at the station 24 so that it can be unreeled to connect its opposite end to grounded transformer housing 14A.

The variable frequency generator and associated means 40 will be described in detail later with respect to FIG. 2. Suffice it for now to state that the means 40 is arranged to impress the selected frequency signal, i.e., the "test signal" via the test lead 48 onto the neutral conductor(s) 10A of the underground cable 10.

Figure 3:
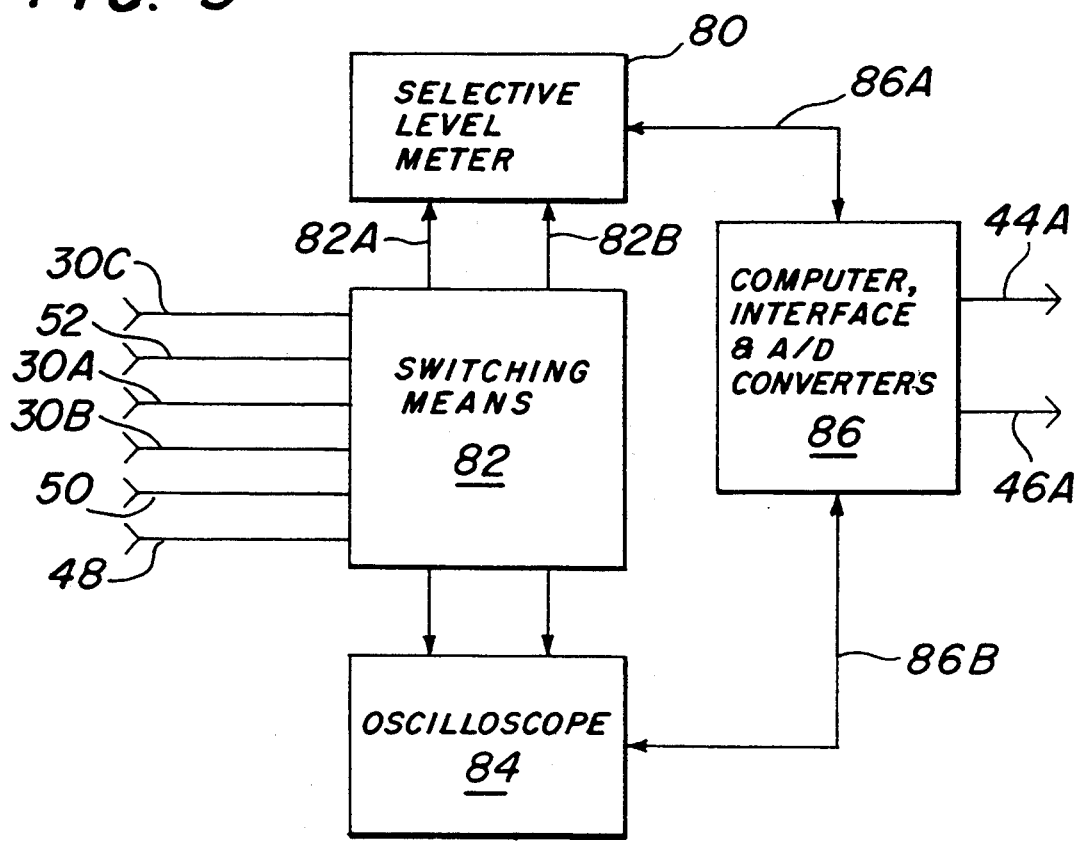
FIG. 3, is a partial schematic and partial functional block diagram of another portion of the system shown in FIG. 1.

The voltage monitoring, computer control, data storage, and processing means 42 will also be described in detail later with respect FIG. 3. Suffice it for now to state that such means is connected to the grounded transformer housing via a conductor 52 and is also connected to the conductors 30A, 30B, and 30C of cable 32 carrying the electrical signals indicative of the shoe-to-shoe potential gradient (also call "step potential") and the DC potential. The means 42 processes those signals, stores various data developed from those processed signals or from other inputs, e.g., keyboard entry, and effects the control of the system 20. The means 42 is connected to a modem 44 to transmit data to some remote location. The printer 46 is connected to the means 42 to provide a printout of the measured potentials or other data.

Figure 2:
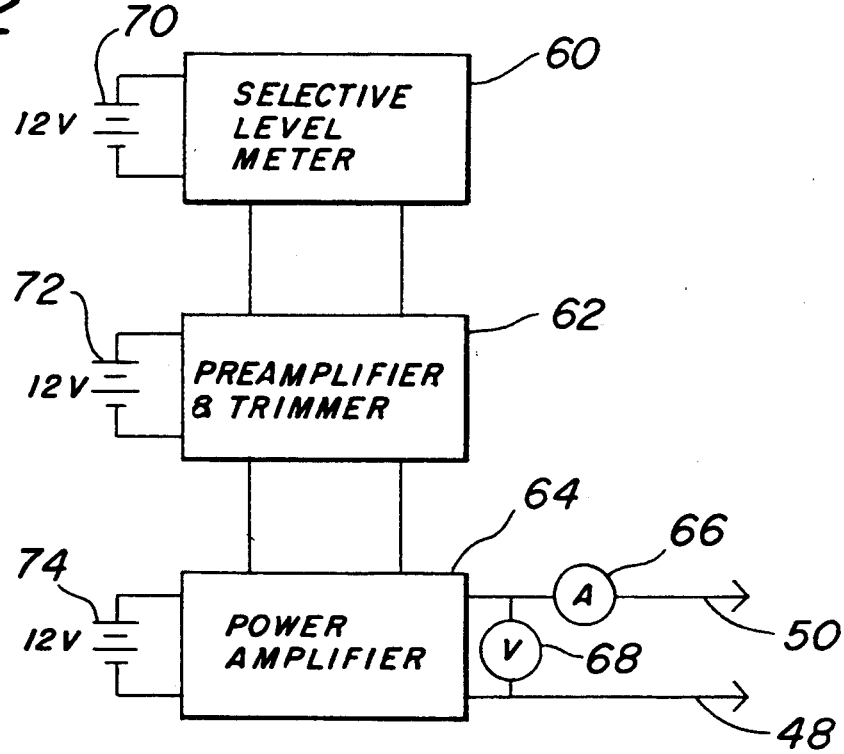
FIG. 2, is a partial schematic and partial functional block diagram of a portion of the system shown in FIG. 1.

Referring to FIG. 2 the details of the variable frequency generator and associated means 40 will now be described. As can be seen therein that means basically comprises a selective level voltmeter or decibel meter 60, a preamplifier and trimmer 62, a power amplifier 64, an ammeter 66, a voltmeter 68, a twelve volt battery 70, a twelve volt battery 72, and a high capacity twelve volt battery 74.

The selective level voltmeter 60 is of any suitable construction, such as made by Rycom Instruments, Inc. of Raytown Mo. 64133, under the model designation R60, and is capable of producing either a sinusoidal or square wave of selectable frequency. The unit 60 is powered both internally and externally by the twelve (12) volt battery 70. That battery is both ground isolated and preferably a lead acid battery. The selective level meter is arranged to be capable of locking onto its own internally produced signal or any other selected frequency. The signal output of the selective level meter 60 is connected to the input of the preamplifier 60. The preamplifier 60 is a universal mono-preamplifier whose output signal is provided to a ten (10) turn trimmer so that it can be controlled as desired. The mono-preamplifier 62 is powered by a twelve volt direct current power supply, i.e., battery 72. The output of the preamplifier/trimmer is provided as the input to the power amplifier 64 and is preferably monitored by a standard panel-mount, broad band voltmeter (not shown). The power amplifier 64 serves as the main power amplifier for the mobile ground potential sensing unit 22 and preferably comprises a 500 watt bridging amplifier. The input power for the main power amplifier 64 is provided by the battery 74, which preferably comprises two (2) to three (3) deep cycle, lead acid batteries. The voltage/current of the batteries making up battery 74 are monitored by broad band amp/volt meters (not shown). The output of the power amplifier, i.e., the test signal, is provided onto conductor (lines) 48 and 50 identified heretofore, and its voltage/current is monitored by the voltmeter 68 and ammeter 66, respectively.

The test signal is selected to be of any desired frequency which is not a harmonic of the native AC on the cable's primary conductor(s) and is preferably in the range of from 20 to 500 Hz. The particular frequency chosen depends upon the dominant harmonic which is determined prior to the survey by use of a power analyzer (not shown). Optimum frequencies have been found to be 80, 220 and 500 Hz. The current magnitude of the test signal is also determined prior to the survey, and ranges from 2 to 15 amperes. The optimum current magnitude is determined by the number of parallel current paths in the distribution system, the cable size, the number of phases, and predicted condition of the neutral conductors. The more numerous the parallel paths, phases and the higher quality of the neutrals generally necessitates increased test currents to produce higher resolution. Conversely, the fewer the parallel paths, phases and poorer neutral condition requires a lower initial selective frequency test current.

The details of the voltage monitoring, computer control, data storage, and processing means 42 of the receiving/monitoring station 24 will now be described with reference to FIG. 3. As can be seen therein the means 42 basically comprises a selective level meter 80, switching means 82, an oscilloscope 84, and a computer and its associated interface and A/D (analog-to-digital) converters 86.

The selective level meter 60 forms a portion of the variable frequency generator 40 described heretofore and is arranged to be locked onto the preset frequency of the variable frequency generator, i.e., the frequency of the test signal. The switching means is of any suitable construction and is arranged to receive three sets of input signals to selectively provide those signals to either the selective level meter 80, via lines 82A and 82B, or the oscilloscope 84, via lines 82C and 82D. Thus, one set of inputs, namely lines 30C and 52 carrying the DC potential measured by the electrode 28 to the grounded transformer housing 12A, is provided to the switching means 82. The second set of inputs to the switching means is provided by lines 30A and 30B carrying the potential gradient between the two shoe electrodes 26A and 26B resulting from the impression of the test signal on the neutral conductors 10A. The third set of inputs to the switching means 82 is provided by lines 50 and 48 carrying the DC potential between the transformer housing 12A and the test conductor.

The output of the selective level meter is provided via a bus 86A to the computer, interface and A/D converter circuitry 86. The output of the oscilloscope is provided via another bus 86B to the circuitry 86. The circuitry 86 is arranged to provide output signals via bus 44A to the modem 44 and via bus 46A to the printer 46.

As can be seen in FIG. 1 the test signal from the selective frequency generator is directly connected to the two structures, e.g., electric power transformers 12 and 14, which are serviced by the underground cable 10 to be tested. A surveyor (not shown) wearing the foot electrodes 26A and 26B on his/her feet, and carrying the copper-copper sulfate reference electrode 28 walks over the ground 16 directly over the path of the electric cable 10 beginning at one transformer, e.g., 12, and traversing the path of the electric cable in a close interval step sequence, e.g., at uniform 2.5 foot paces, until he/she arrives at the second or adjacent transformer, e.g., 14. The shielded test cable 32 is unreeled during the course of the survey and is of sufficient length so as to traverse the distance between the station 24 and the transformer 14.

At each step that the surveyor takes between the transformers the copper-copper sulfate electrode 28 is brought into engagement with the ground under the surveyor's feet and direct current (DC) potentials are monitored between the copper-copper sulfate electrode and the transformer ground by the voltage monitoring and associated means 42 in the station 24. In addition the potentials between the surveyor's foot electrodes at the selected, i.e., test frequency, is monitored by the voltage monitoring and associated means 42, along with the native alternating current (AC) potentials between those electrodes. All of these measurements are made by the meter 80 under computer control or manually at the particular frequency being monitored, e.g., the frequency of the test signal, the frequency of the native AC or harmonics thereof. Alternatively one or more additional voltmeters can be used in conjunction with the voltmeter 60 to measure the various potentials. In any event these measurements are recorded by a computer forming a portion of the voltage monitoring and associated means 42. Alternatively, a digital data logger may be used to record the measurements. In any case, at all points of direct current or selective frequency potential abnormalities, a waveform is recorded of both potentials as well as peak-to-peak potential measurements, maximum potential, minimum potential, mean potential, frequency, RMS voltage and soil resistivity. Soil resistivity is measured using any conventional technique, e.g., the Wenner Four-Pin method at depths of 2.5, 5.0 and 7.5 feet.

Landmarks and control of the survey progression is controlled remotely from the surveyor by another person (not shown) who located at and operates the station 24. The operator of the station 24 and the surveyor preferably communicate with each other via voice activated radios (not shown). At areas of abnormal direct current potential measurements and/or selective frequency measurements, both step and potential waveform recordings are made, as well as a harmonic sweep of the applied selective frequency and background 60 hertz current. These waveforms and harmonics are digitally recorded by the means 42 for further analysis. The length and depth of the area of abnormality are referenced to permanent land features.

At the end of every survey section, measurements of voltage drops are made between the transformers 12 and 14 under the area of testing. These measurements are made by directly contacting the transformer vault or pad housing and measuring the voltage difference between them. The voltage difference is measured by a DC broad band meter, and the selective frequency voltmeter set at the test current. Harmonic voltage measurements are made set at the dominant AC harmonics for the line under test. A waveform is also recorded of the broad band harmonic.

Prior to testing the underground electric cable 10 coupled to the selective level meter 60 tuned to the frequency of the test current and the cable path is marked from transformer 12 to transformer 14. At all paved driveways, roads and walkways a stainless steel electrode is inserted in the earth on the opposite side of the paved area from the direction of the survey. A jumper wire is run across the pavement to the earth contact electrode. Measuring tapes are then laid over the path of the cable from transformer to transformer.

After completing the setup procedures, cable locating and distance measuring the survey begins in a step fashion from transformer 12 to transformer 14. At each 2.5 foot interval step, impressed selective frequency current potentials and native AC current are measured between the foot electrodes and a direct current potential is also recorded between the reference electrode and the cable neutrals. These readings are monitored and recorded by the computer remotely. After the readings are auto-entered into the computer the equipment operator or computer radios the surveyor to continue. At each permanent land mark feature and/or 100 foot interval the surveyor radios the information back to the equipment operator for entry with the locations voltage measurements.

At any location of apparent anomalies in the cable readings a waveform analysis is conducted to determine the harmonic spectrum of both the native and selective frequency voltages. These measurements are recorded for both the step and structure-to-reference electrode voltages. The distance and closest permanent land feature are also recorded. After completion of the digital logging of these readings the survey continues.

At all paved locations a single step and direct current voltage is recorded across the structure. The step voltage is accomplished by measuring the voltage drop between the inserted stainless steel pins installed prior to the beginning of the survey and one of the foot electrodes. The length of the paved area is also measured. After completion of the digital logging of these readings the survey continues.

Upon completion of the survey a series of current/resistance measurements are conducted. These readings are referred to as IR drop measurements. The surveyor contacts the structure with one foot electrode and an overall IR drop direct current and selective frequency voltage is measured. Also a waveform analysis is conducted to determine the harmonic spectrum of both the native and selective frequency voltages at each of the transformers under test.

During the testing, soil resistivity measurements are conducted at each transformer and areas of apparent corrosion abnormalities. Soil resistivities are measured by the Wenner Four-Pin method at depths of 2.5, 5.0 and 7.5 feet. This data is recorded and auto analyzed using the Barnes Parallel Layer Resistance method. The cables are moved to the next set of transformers and the next section is begun.

Prior to the beginning of the next survey section the data may be processed and printed graphically in the field for presentation and analysis. The 2.5 foot interval step voltages and direct current potential distance were chosen to provide sufficient data for a continuous voltage profile. This profile is graphically plotted on a dual axis XY graph. The graphics presentation is useful in analysis of the underground neutral condition.

In accordance with this invention an analysis of the data point relationships, harmonic power analysis and soil resistivity may be conducted either manually from the graphic presentation and data and/or by expert computer software to determine the following: neutral discontinuity, ungrounded drop poles, areas of active corrosion, cable repair splices, areas of semiconductor damage, locations of bimetallic corrosion cells with parallel or intersecting foreign structures, areas free of corrosion activity, galvanic corrosion cell locations, areas of direct current electrolytic corrosion activity, locations of either semiconductor and/or cuprous oxide half wave rectification, locations and types and sources of harmonic activity, modeling of semiconductor harmonic activity sources, locations requiring cable replacement, other non-drop pole grounding anomalies, locations of non-corrosion related neutral damage, neutral locations requiring cathodic protection, areas of neutral tinning loss, areas of corrosion activity not necessitating cable replacement, areas requiring neutral repair, cathodic protection groundbed locations, locations of parallel ground current paths, determination of galvanic or impressed current cathodic protection, areas and foreign structures prone to induced AC activity, permanent land feature correlations with cable locations, transformer grounding conditions, and soil corrosivity As should be appreciated from the foregoing the system of this invention enables testing underground electric cables while in service for active corrosion and degree of neutral loss at precise locations utilizing preset selective frequency alternating currents. In addition to active corrosion and neutral loss the system and its method of use pinpoints all grounding abnormalities, harmonics and waveform distortions on underground bare neutral electric cable. Accordingly, the system and method of use provides all data necessary in a one pass survey for a complete evaluation of the condition of the underground electric cable system.

Without further elaboration the foregoing will so fully illustrate our invention that others may, by applying current or future knowledge, adopt the same for use under various conditions of service.

We claim:

1. A method for non-intrusively testing the status of corrosion of a neutral conductor of an underground electrical cable forming a portion of an electrical power system, said cable additionally comprising at least one primary conductor carrying AC current therethrough when said cable is in service providing normal electrical power to said power system, said neutral conductor of said cable surrounding said at least one primary conductor and being connected between a pair of electrically grounded structures, said method for testing being accomplished while leaving said cable in normal operation and comprising the steps of:
   (a) impressing an electrical test signal of a predetermined frequency between said grounded structures while said cable is in service providing normal electrical power to said power system via said primary conductor to impress said test signal on said neutral conductor while leaving said neutral conductor connected to said structures so that said neutral conductor remains grounded,
   (b) causing a pair of electrically conductive probes to contact the ground located over said underground cable at predetermined spaced intervals while said test signal is impressed on said neutral conductor, and
   (c) measuring the voltage gradients produced by said test signal in the ground by using monitoring means coupled to said spaced electrically conductive probes while said probes are in contact with the ground and while said primary conductor is carrying said AC current therethrough.

2. The method of claim 1 additionally comprising the step of measuring the resistivity of the ground at selected locations above said underground cable.

3. The method of claim 1 additionally comprising the step of measuring the native AC ground voltages produced by said AC current in said primary conductor at said predetermined spaced intervals.

4. The method of claim 1 wherein said measured voltage gradients are utilized to provide an indication of abnormalities in the underground cable.

5. The method of claim 1 additionally comprising the step of measuring the resistivity of the ground at selected locations above said underground cable, measuring the native AC ground voltages produced by said AC current in said primary conductor at said predetermined spaced intervals, and measuring the DC potentials at said predetermined spaced intervals.

6. The method of claim 1 additionally comprising recording said measured voltage gradients.

7. A non-intrusive testing system for determining the status of corrosion of a neutral conductor of an underground electrical cable forming a portion of an electrical power system, said cable additionally comprising at least one primary conductor carrying AC current therethrough when said cable is in service providing normal electrical power to said power system, said neutral conductor of said cable surrounding said at least one primary conductor and being connected between a pair of electrically grounded structures, said testing system being arranged for use with said cable while said cable is in normal operation and comprising:
   (a) first means for impressing an electrical test signal of a predetermined frequency between said grounded structures while said cable is in service providing normal electrical power to said power system to impress said test signal on said neutral conductor while leaving said neutral conductor connected to said structures so that said neutral conductor remains grounded,
   (b) a pair of electrically conductive probes arranged to be brought into contact with the ground located over said underground cable at predetermined spaced intervals while said test signal is impressed on said neutral conductor, and
   (c) monitoring means coupled to said pair of electrically conductive probes for measuring the voltage gradients produced by said test signal in the ground while said probes are in contact with the ground and while said primary conductor is carrying said AC current therethrough.

8. The system of claim 7 additionally comprising means for recording said measured voltage gradients.

9. The system of claim 7 wherein said probes are arranged to be mounted on the feet of a person.

10. The system of claim 7 additionally comprising electrode means for measuring the DC potential at said predetermined spaced intervals.

11. The system of claim 7 wherein said monitoring means measures the rms voltage and the peak-to-peak voltage of said gradient.

12. The system of claim 7 wherein said monitoring means is located in a vehicle arranged to traverse the ground adjacent the path of said underground cable.

13. A method for non-intrusively testing the status of corrosion of a neutral conductor of an underground electrical cable forming a portion of an electrical system, said cable additionally comprising at least one primary conductor carrying AC current therethrough when said cable is in service in said electrical system, said neutral conductor of said cable being connected between a pair of electrically grounded structures, said method for testing being accomplished while leaving said cable in normal operation and comprising the steps of:
(a) impressing an electrical test signal of a predetermined frequency on said neutral conductor between said structures while said cable is in service to impress said test signal on said neutral conductor while leaving said neutral conductor connected to said structures,
(b) causing a pair of electrically conductive probes to contact the ground located over said underground cable at predetermined spaced intervals while said test signal is impressed on said neutral conductor, and
(c) measuring the voltage gradients produced by said test signal in the ground by using monitoring means coupled to said spaced electrically conductive probes while said probes are in contact with the ground and while said primary conductor is carrying said AC current therethrough.

14. The method of claim 13 additionally comprising the step of measuring the resistivity of the ground at selected locations above said underground cable.

15. The method of claim 13 wherein said measured voltage gradients are utilized to provide an indication of abnormalities in the underground cable.

16. The method of claim 13 additionally comprising recording said measured voltage gradients.

17. The method of claim 13 wherein said neutral conductor surrounds said at least one primary conductor.

18. A non-intrusive testing system for determining the status of corrosion of a neutral conductor of an underground electrical cable forming a portion of an electrical system, said cable additionally comprising at least one primary conductor carrying AC current therethrough when said cable is in service in said electrical system, said neutral conductor of said cable being connected between a pair of electrically grounded structures, said testing system being arranged for use with said cable while said cable is in normal operation and comprising:
(a) first means for impressing an electrical test signal of a predetermined frequency between said structures while said cable is in service to impress said test signal on said neutral conductor while leaving said neutral conductor connected to said structures,
(b) a pair of electrically conductive probes arranged to be brought into contact with the ground located over said underground cable at predetermined spaced intervals while said test signal is impressed on said neutral conductor, and
(c) monitoring means coupled to said pair of electrically conductive probes for measuring the voltage gradients produced by said test signal in the ground while said probes are in contact with the ground and while said primary conductor is carrying said AC current therethrough.

19. The system of claim 18 additionally comprising means for recording said measured voltage gradients.

20. The system of claim 18 wherein said probes are arranged to be mounted on the feet of a person.

21. The system of claim 18 additionally comprising electrode means for measuring the DC potential at said predetermined spaced intervals.

22. The system of claim 18 wherein said monitoring means measures the rms voltage and the peak-to-peak voltage of said gradient.

23. The system of claim 18 wherein said monitoring means is located in a vehicle arranged to traverse the ground adjacent the path of said underground cable.

24. The system of claim 18 wherein said neutral conductor surrounds said at least one primary conductor.

* * * * *